(12) United States Patent
Amron

(10) Patent No.: US 9,326,593 B2
(45) Date of Patent: May 3, 2016

(54) FOUNTAIN TOOTHBRUSH

(71) Applicant: Scott Amron, Smithtown, NY (US)

(72) Inventor: Scott Amron, Smithtown, NY (US)

( * ) Notice: Subject to any disclaimer, the term of this patent is extended or adjusted under 35 U.S.C. 154(b) by 92 days.

(21) Appl. No.: 14/349,609

(22) PCT Filed: Oct. 3, 2012

(86) PCT No.: PCT/US2012/000490
§ 371 (c)(1),
(2) Date: Apr. 3, 2014

(87) PCT Pub. No.: WO2013/052125
PCT Pub. Date: Apr. 11, 2013

(65) Prior Publication Data
US 2014/0237741 A1    Aug. 28, 2014

Related U.S. Application Data

(60) Provisional application No. 61/626,863, filed on Oct. 3, 2011.

(51) Int. Cl.
*A46B 11/00* (2006.01)
*A46B 15/00* (2006.01)
*A61C 17/02* (2006.01)

(52) U.S. Cl.
CPC ......... *A46B 11/0072* (2013.01); *A46B 15/0067* (2013.01); *A46B 2200/1066* (2013.01); *A61C 17/0202* (2013.01)

(58) Field of Classification Search
CPC .............. A61C 17/02; A61C 17/0202; A46B 15/0055; A46B 15/0067; A46B 11/00; A46B 11/0202; E03B 9/00; E03B 9/20; B05B 12/00; B05B 17/08

USPC ....... 15/4, 105; 239/24; 401/188 R, 268, 270, 401/282–291; 601/154, 160, 162
See application file for complete search history.

(56) References Cited

U.S. PATENT DOCUMENTS 2,154,209 A * 4/1939 Kohn ..................... A46B 15/00
                                                        15/105
2,956,749 A * 10/1960 Perry ..................... A46B 11/06
                                                        15/105

(Continued)

FOREIGN PATENT DOCUMENTS

EP            0097015 A2    12/1983
JP            S36024313     9/1936

(Continued)

OTHER PUBLICATIONS

Japanese Patent Office, English translation of Office Action dated Jun. 2, 2015, 6 pgs.

(Continued)

*Primary Examiner* — Mark Spisich
(74) *Attorney, Agent, or Firm* — Lucas & Mercanti, LLP

(57) ABSTRACT

A toothbrush includes a housing having a handle and a toothbrush head, a pump having a pump chamber and a pump impeller or pump gear arranged in the pump chamber, and a motor driving the impeller or pump gear. An input port and an output port are connected to the chamber, the impeller causing a flow of a working fluid through the output port when the impeller is driven by the motor and the working fluid is supplied through the input port. The pump chamber has a circumferential wall defining a transverse cross section, the output port being connected to the pump chamber through the circumferential wall.

18 Claims, 5 Drawing Sheets

(56) References Cited

U.S. PATENT DOCUMENTS

| | | | |
|---|---|---|---|
| 3,361,355 A * | 1/1968 | Renee | A46B 15/0055 15/105 |
| 3,504,852 A * | 4/1970 | Abbott | A46B 11/06 15/105 |
| 3,869,746 A | 3/1975 | Man-king | |
| 4,429,434 A | 2/1984 | Sung-shan | |
| 6,164,967 A | 12/2000 | Sale | |
| 6,245,032 B1 | 6/2001 | Sauer | |
| 7,607,851 B2 | 10/2009 | Amron | |
| 7,905,674 B2 | 3/2011 | Amron | |
| 2008/0050695 A1 | 2/2008 | Amron | |
| 2008/0196184 A1 | 8/2008 | Dooley | |
| 2011/0070016 A1 | 3/2011 | Richardson | |

FOREIGN PATENT DOCUMENTS

| | | |
|---|---|---|
| JP | S62148661 A | 7/1987 |
| JP | H05041517 | 6/1993 |
| JP | H04069666 | 7/1993 |
| JP | H06019563 U | 3/1994 |
| JP | H08308641 A | 11/1996 |
| JP | 2004041687 A | 2/2004 |
| JP | 2006061877 A | 3/2006 |
| KR | 20-0374492 Y1 | 1/2005 |

OTHER PUBLICATIONS

European Patent Office, Office Action dated May 21, 2015 with European Search Report dated May 4, 2015, 6 pgs.
State Intellectual Property Office, Peoples Republic of China, English translation of Office Action fated Feb. 25, 2015, 12 pgs.
Canadian Patent Office, Office Action dated Aug. 5, 2015, 4 pgs.
Australian Patent Office, Patent Examination Report No. 1, dated Oct. 10, 2104, 3 pgs.
Australian Patent Office, Patent Examination Report No. 2, dated Oct. 1, 2105, 3 pgs.
Korean Intellectual Property Office, English translation of Notice of Preliminary Rejection dated May 11, 2015, 5 pgs.

* cited by examiner

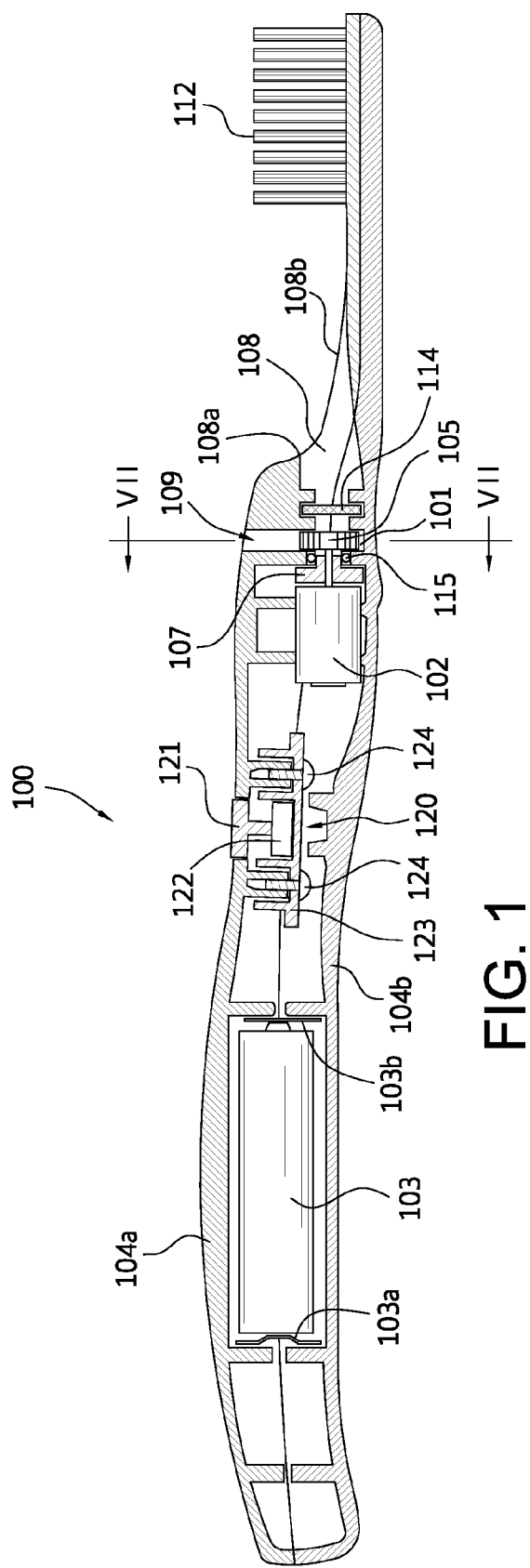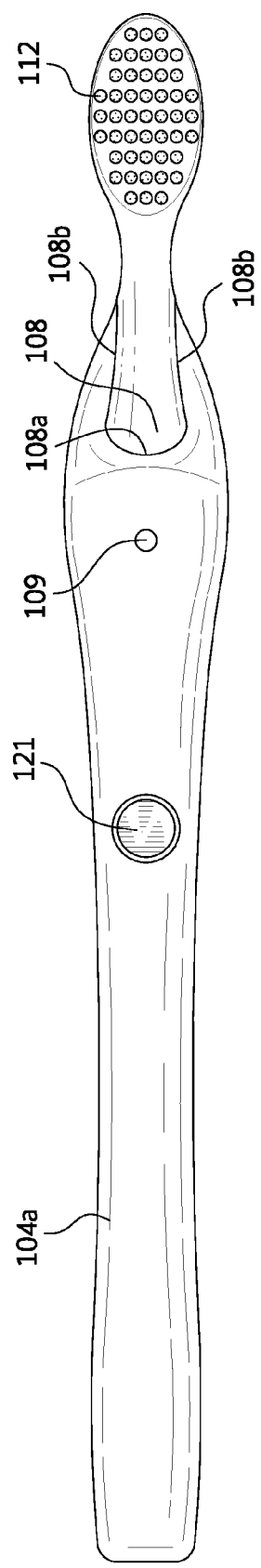
FIG. 1
FIG. 2

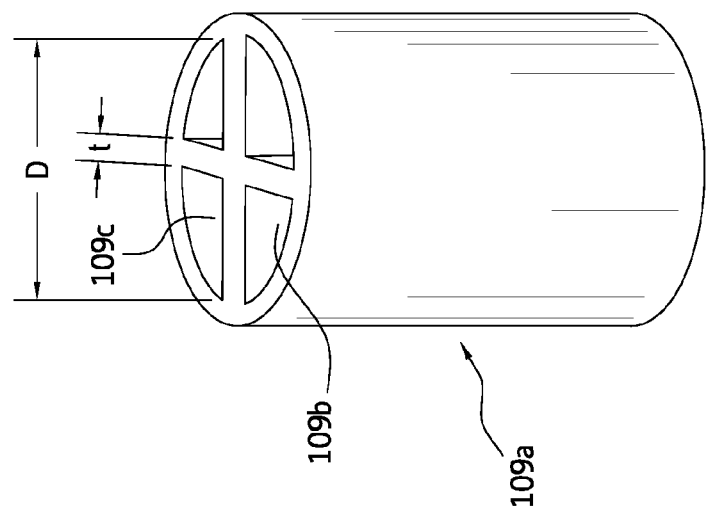
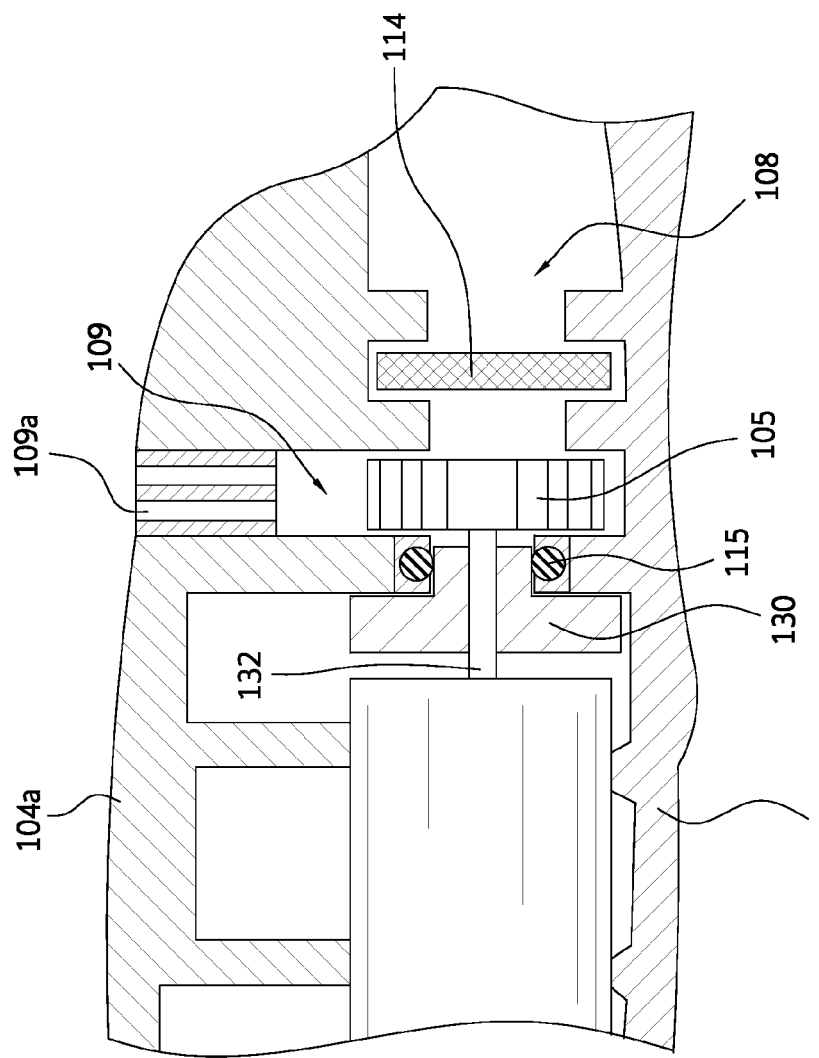

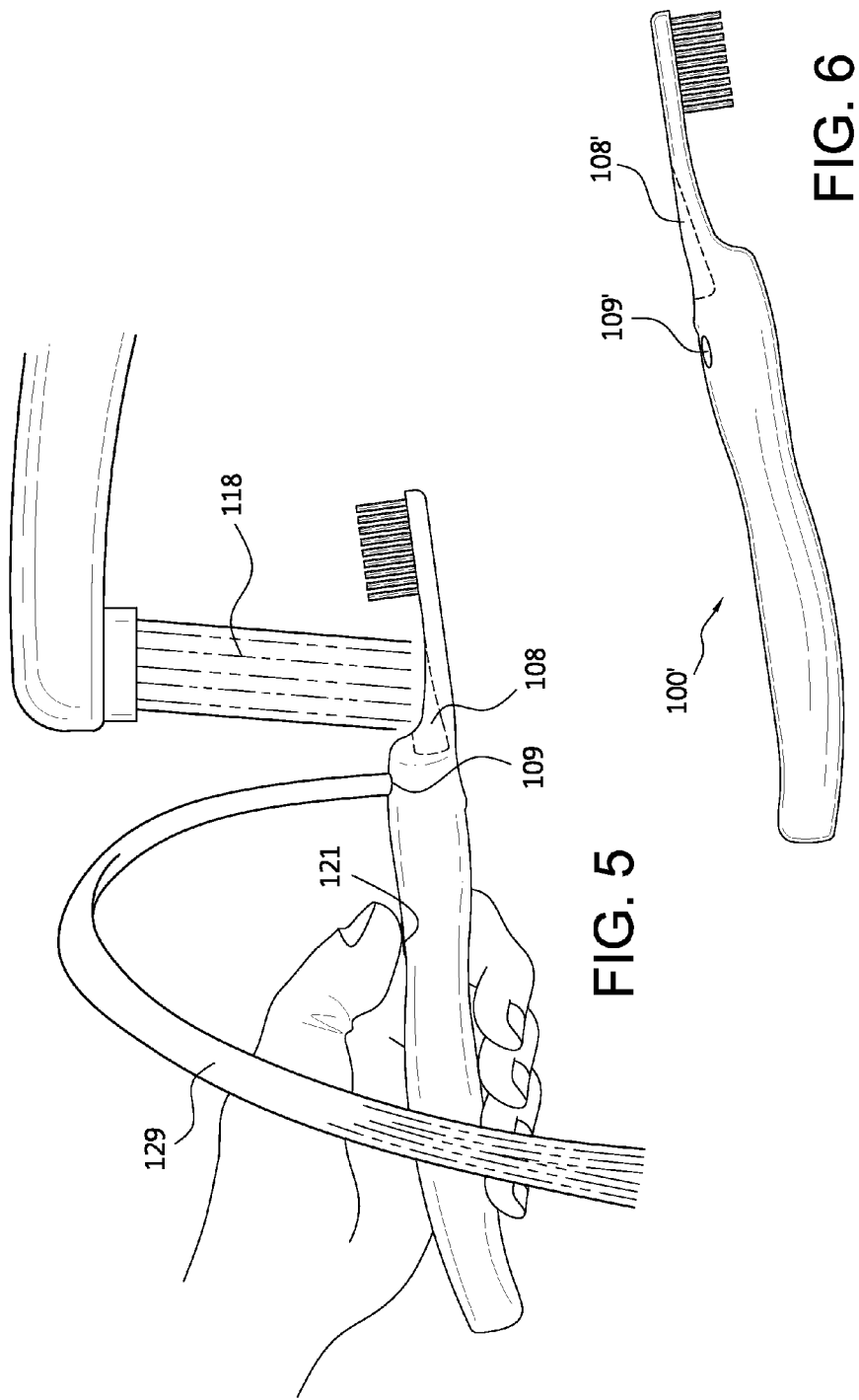

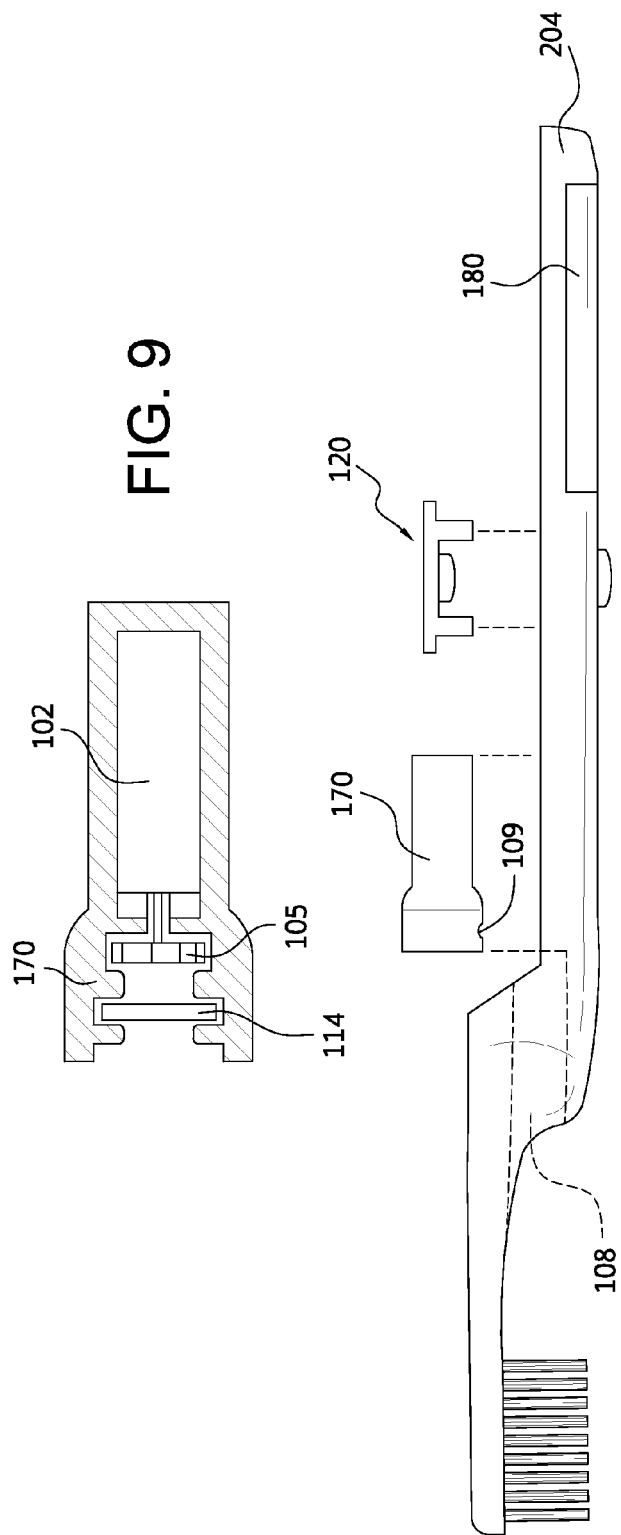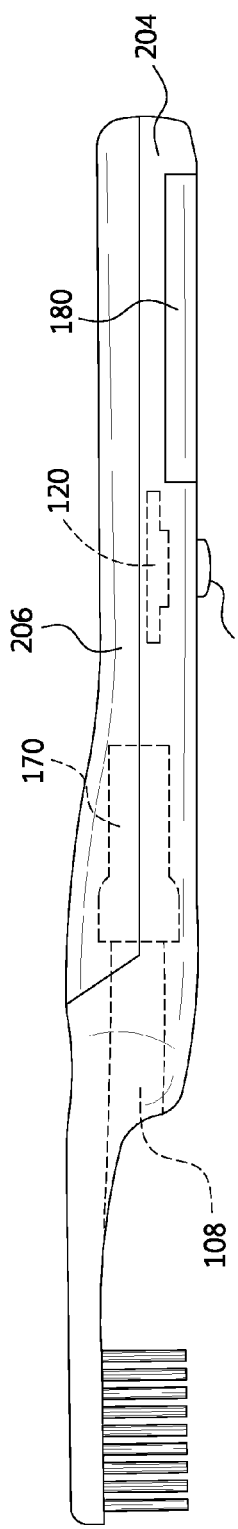

FOUNTAIN TOOTHBRUSH

The present invention claims priority to U.S. Provisional Application No. 61/626,863 filed Oct. 3, 2011, the contents of which are hereby incorporated in their entirety.

BACKGROUND OF THE INVENTION

1. Field of the Invention

The present invention relates to a manual toothbrush for brushing teeth with a pump configured to receive and redirect water from a faucet into a fountain stream for rinsing after brushing teeth.

2. Description of Prior Art

Brushing teeth is an essential part of any oral hygiene routine. However, if a person is not at home, a cup may not be available for oral rinsing after brushing. Furthermore, even if a cup is available, cups collect dirt and require frequent cleaning. The use of paper cups solves the problem of cleaning but is not environmentally friendly as it creates waste. Water directly from a faucet may also be used, but it is difficult to get the water from the faucet to a person's mouth without a cup. It is difficult to carry enough water for rinsing in cupped hands and it is even more difficult to obtain the water directly into a user's mouth from the faucet.

U.S. Pat. Nos. 7,607,851 and 7,905,674, by the inventor of the present application, disclose fountain toothbrushes that include open or closed channels on the toothbrush housing to redirect water from a faucet back to the user in the form of a fountain. These channels are passive in that they depend at least in part on the strength of the flow discharged from the faucet.

SUMMARY OF THE INVENTION

An object of the present invention is to provide a toothbrush that facilitates oral rinsing.

The object is met by a toothbrush including a housing having a handle and a toothbrush head, a pump having a pump chamber and a pump impeller or pump gear arranged in the pump chamber, and a motor driving the impeller or pump gear. An input port and an output port are connected to the chamber, the impeller causing a flow of a working fluid through the output port when the impeller is driven by the motor and the working fluid is supplied through the input port. The pump chamber has a circumferential wall defining a transverse cross section of the pump casing, the output port being connected to the pump chamber through the circumferential wall.

The output port includes a plurality of parallel channels according to one embodiment of the invention. The channels are separated by fins that extend longitudinally through the output port. The output port has an overall diameter of approximately 3.25 mm. The fins may be injection molded as part of the housing. Alternatively, the fins may be part of an extruded part that is inserted into the output port. In one specific embodiment, the fins include at least two fins that are perpendicular to each other.

According to an embodiment, the pump is a centrifugal pump. In this embodiment, the output port extends radially outward from the circumferential wall with respect to a rotating axis of the impeller.

According to another embodiment, the output port extends perpendicular to the circumferential wall at the area in which the output port is connected to the chamber.

The input port may be covered with a filter. The filter may, for example, be a plastic screen or a plastic grating.

The toothbrush according to another embodiment may further include a switch for starting and stopping the motor. The switch is preferably a momentary switch that turns on the motor when pressed and turns off the motor when released.

According to another embodiment, the input port comprises a channel configured to receive water flowing from a faucet and is on a same side of the housing as the output port.

According to another embodiment, the housing comprises two injection molded parts, defining an upper part and a lower part of the pump chamber respectively.

According to another embodiment, at least the motor the impeller are arranged in a pump casing, wherein the pump casing is inserted into the housing as a unit and overmolded in place by an overmolding material. The switch may also be inserted into the housing and overmolded in place.

BRIEF DESCRIPTION OF THE DRAWINGS

The various features, functions, and advantages characterizing the invention will be better understood by reference to the detailed description which follows, when viewing the accompanying drawings, in which:

FIG. 1 is a longitudinal sectional view of a toothbrush according to an embodiment of the present invention;

FIG. 2 is a plan view of the toothbrush of FIG. 1;

FIG. 3 is a detailed sectional view of the components proximate a pump chamber in the toothbrush of FIG. 1;

FIG. 4 is a perspective view of an insert for the input port for the pump chamber of FIG. 3;

FIG. 5 is a perspective view of the toothbrush of FIG. 1 during use;

FIG. 6 is a perspective view of another embodiment of the toothbrush according to the present invention;

FIG. 9 is a longitudinal sectional view of a pump casing according to another embodiment of the present invention;

FIG. 10 is an exploded view of a toothbrush with the pump casing of FIG. 9; and

FIG. 11 is a view of the toothbrush of FIG. 10 with the pump casing overmolded in place.

DETAILED DESCRIPTION OF THE PREFERRED EMBODIMENTS

Figure 8:
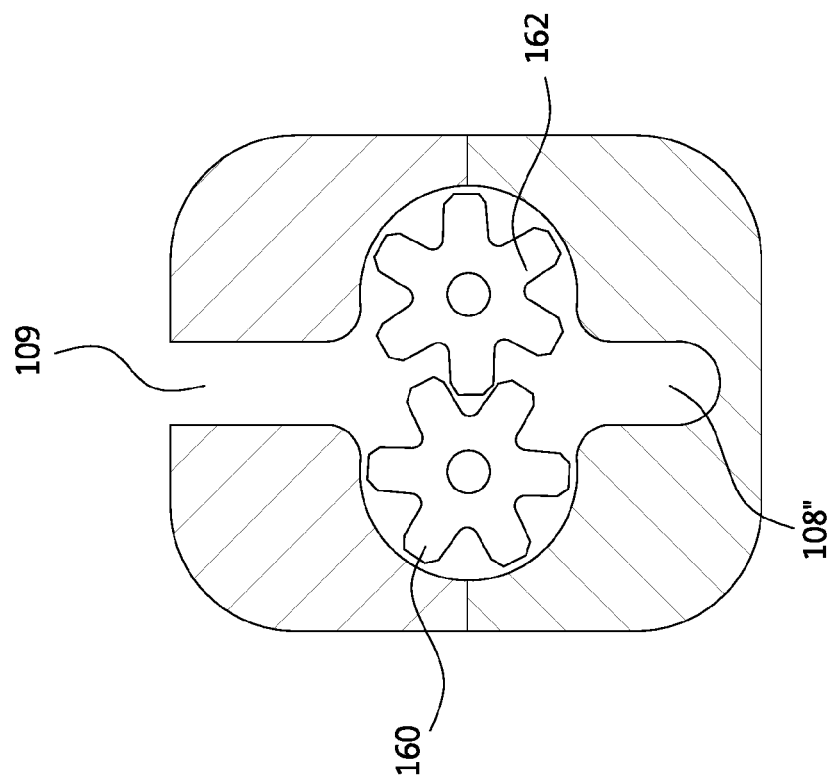
FIG. 8 is a sectional view of the pump chamber according to a further embodiment of the present invention.

A toothbrush 100 according to an embodiment of the present invention is shown in FIG. 1. The toothbrush 100 has a housing 104 that includes an upper housing 104a and a lower housing 104b. Toothbrush bristles 112 are arranged at a head portion of the toothbrush. The housing 104 defines a pump chamber 101 accommodating an impeller 105, which is connected to a motor 102. The motor 102 drives the impeller 105 to rotate and the impeller draws water from an input port 108 and ejects water through an output port 109, as will be described in more detail below. The motor 102 comprises a coreless DC motor such as model 615 or 716.

A battery 103 is arranged between two electric contacts 103a, 103b in the housing 104 and is connected to the motor 102 through a switch 122. According to the present embodiment, the switch 122 is a momentary tactile switch that activates the motor when the switch is pressed and turns off the motor 102 upon release of pressure from the switch 122. Although a momentary tactile switch is used in the present embodiment, any other type of electrical switch could be used to turn the motor 102 on and off. The switch 122 is arranged on a switch assembly 120, which includes a printed circuit board (PCB) base 123 on which the switch 122 is mounted. The base 123 is connected to the upper housing 104a using connecting elements such as threaded fasteners 124, i.e., screws or bolts. A pushbutton 121 is mounted on the switch assembly 120 or on the upper housing 104a and is manipulated by a user to activate the switch 122.

FIG. 2 is a plan view showing the relative locations of the input port 108, the output port 109, and the pushbutton 121 on the upper housing 104a of the toothbrush. The input port 108 includes an upper rim portion 108a and side rim portions 108b. Accordingly, the input port 108 is designed to guide or direct any water that strikes the upper housing 104a of the toothbrush 100 between the bristles 112 and the upper rim 108a into the pump chamber 101.

FIG. 3 is a more detailed view of the pump chamber 101 and surrounding components. The impeller 105 is arranged in the pump chamber 101 and is mounted on a motor shaft 132, or a shaft drivably connected to the motor shaft, and is rotated by the motor 102. The rotation of the impeller 105 causes water in the chamber 101 to be ejected through the output port 109. The rotation of the impeller 105 also draws water into the chamber 101. As shown in FIG. 3, the motor shaft 132 is inserted through a collar or bushing 130. A seal 115 between the bushing 130 and the housing 104 prevents water from exiting the pump chamber 101. The motor seal between the bushing 130 and the housing 104 and/or between the bushing 130 and the motor shaft 132 is packed with food safe DOW 111 lubricant.

As shown in FIG. 3, a filter 114 is arranged between the input port 108 and the chamber 101. The filter 114 is in the form of a grating and is made, e.g., from injection molded plastic and/or rubber. The filter 114 prevents large objects from entering the pump chamber 101 to prevent damage to the impeller and to prevent injury to a user. In addition, the output port 109 includes an insert 109a (see also FIG. 4) with longitudinal fins 109b that separate the output port into a plurality of channels 109c. The insert can be an extruded plastic, i.e., food safe PVC, with a fin thickness t no greater than 1 mm. It is preferred that the fin thickness t is not greater than 0.65 mm. In a most preferred embodiment, the fin thickness t is less than or equal to 0.2 mm. The overall diameter D of the output port 109 is not greater than 5 mm and is preferably approximately 3.25 mm. All parameters are approximate and may vary based on manufacturing tolerances.

The insert 109a as shown in FIGS. 3 and 4 may extend through part of the length of the output port 109. However the fins 109b should extend at least one half of the length of the output port 109. The fins 109b and channels 109c facilitate the formation of a fountain of water flow out of the output port 109 in a fountain. Without the insert 109a, the water spreads more is not in the form of a fountain. Instead of using an insert 109a, the fins 109b could be molded into the upper housing 104a.

FIG. 5 illustrates the intended use of the toothbrush 100. A user hold the toothbrush 100 so that a stream of water 118 from a faucet enters the input port 108. As shown in FIG. 5, the user's thumb presses pushbutton 121 to activate the motor and the pump ejects a fountain 129 of water from the output port 109.

FIG. 6 shows an alternative embodiment in which the input port 108' and output port 109' open on the lower side of the toothbrush 100'. In both the FIG. 1 and FIG. 6 embodiments, the pushbutton 121 for activating the switch may be arranged on the same side of the toothbrush as the housing or on the opposite side.

Figure 7:
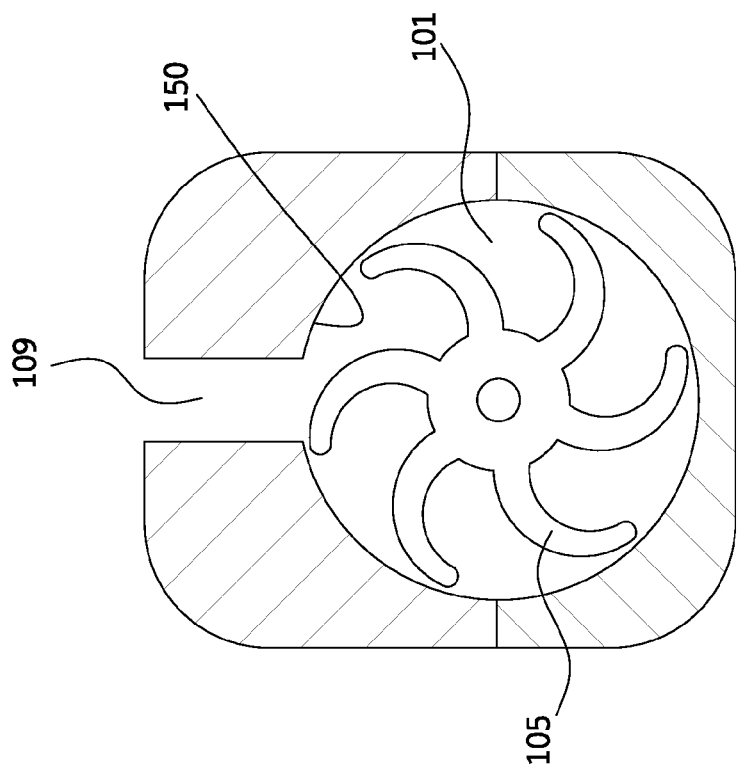
FIG. 7 is a sectional view of the pump chamber of FIG. 1.

FIG. 7 is a sectional view of the pump chamber 101 shown in FIG. 1. The circumferential wall 150 of the pump chamber 101 is circular. The water to be pumped enters the chamber 101 axially through the input port 108 and exits radially through the output port 109. The impeller 105 in FIG. 7 is depicted as an impeller of a centrifugal pump. The output port of a centrifugal pump is normally arranged tangential to the circumference of the pump chamber. However, for the purposes of the toothbrush body, it is better to be in the middle of the top of the toothbrush.

FIG. 8 shows an alternative embodiment using a gear pump. The gear pump includes a drive gear 160 and an idler gear 162. Water enters a suction port, i.e., input port 108" from a front of the pump and ejects water out of the output port 109. Here the axis of the drive gear is offset from a center of the toothbrush. Thus, the motor will have to be connected by a gear so that the motor is in the middle of the toothbrush.

FIG. 9 shows a further embodiment in which the motor 102, the impeller 105, and the filter 114 are arranged in a pump casing 170. Here the bushing 130 is not required because stresses are absorbed by the pump casing during installation. As shown in FIG. 10, the pump casing can be installed into a housing piece 204 as a unit. Likewise, the switch assembly 120 can be installed into the housing piece 204. Once installed, the pump casing 170 and the switch assembly can be overmolded by a injection molded material 206. In the embodiments of FIGS. 10 and 11, the housing includes a removable battery cover 180. The cover 180 may alternatively comprise an opening at an end of the of the toothbrush.

The present invention has been described with reference to a preferred embodiments. It should be understood that the scope of the present invention is defined by the claims and is not intended to be limited to the specific embodiments disclosed herein. For example, elements of specific embodiments may be used with other embodiments without deviating from the scope of the present invention.

What is claimed is:

1. A toothbrush, comprising:
a housing having a handle and a toothbrush head;
a pump having a pump chamber and a pump impeller or pump gear arranged in the pump chamber;
a motor driving the impeller or pump gear; and
an input port and an output port connected to the chamber, the impeller or pump gear causing a flow of a working fluid through the output port when the impeller or pump gear is driven by the motor and the working fluid is supplied through the input port, whereby a stream of fluid exits the output port for oral rinsing, the pump chamber having a circumferential wall defining a transverse cross sectional shape of the pump chamber, the output port being connected to the pump chamber through the circumferential wall.

2. The toothbrush of claim 1, wherein the output port includes at least one longitudinal web for directing a flow of working fluid through the output port.

3. The toothbrush of claim 2, wherein the at least one web divides the output port into a plurality of channels separated by the at least one web.

4. The toothbrush of claim 3, wherein the at least one web is injection molded as part of the housing.

5. The toothbrush of claim 3, wherein the at least one web is part of an extruded part that is inserted into the output port.

6. The toothbrush of claim 3, wherein the at least one web includes at least two walls that are perpendicular to each other.

7. The toothbrush of claim 2, wherein the output port has an overall diameter of approximately 3.25 mm.

8. The toothbrush of claim 1, wherein the pump is a centrifugal pump.

9. The toothbrush of claim 8, wherein the output port extends radially outward from the circumferential wall with respect to a rotating axis of the impeller.

10. The toothbrush of claim 1, wherein the output port extends perpendicular to the circumferential wall at the area in which the output port is connected to the chamber.

11. The toothbrush of claim 1, wherein the input port is covered with a filter.

12. The toothbrush of claim 11, therein the filter is a plastic screen, a plastic grating, or a rubber with a high durometer value.

13. The toothbrush of claim 1, further comprising a switch for starting and stopping the motor.

14. The toothbrush of claim 13, wherein the switch is a momentary switch that turns on the motor when pressed and turns off the motor when released.

15. The toothbrush of claim 13, wherein at least the motor and the impeller are arranged in a pump casing, wherein the pump casing and the switch are inserted into the housing and overmolded in place.

16. The toothbrush of claim 1, wherein the input port comprises a channel configured to receive water flowing from a faucet and is on a same side of the housing as the output port.

17. The toothbrush of claim 1, wherein the housing comprises two injection molded parts, defining an upper part and a lower part of the pump chamber respectively.

18. The toothbrush of claim 1, wherein at least the motor and the impeller are arranged in a pump casing, wherein the pump casing is inserted into the housing and overmolded in place.

* * * * *